(12) United States Patent
Matsuo et al.

(10) Patent No.: US 9,138,020 B2
(45) Date of Patent: Sep. 22, 2015

(54) KNEE JOINT SUPPORTER (75) Inventors: Kazuhiko Matsuo, Tokyo (JP); Hidefumi Koga, Gose (JP)

(73) Assignee: Kowa Company, LTD., Tokyo (JP)

( * ) Notice: Subject to any disclaimer, the term of this patent is extended or adjusted under 35 U.S.C. 154(b) by 224 days.

(21) Appl. No.: 13/522,666

(22) PCT Filed: Jan. 24, 2011

(86) PCT No.: PCT/JP2011/051220
§ 371 (c)(1),
(2), (4) Date: Jul. 17, 2012

(87) PCT Pub. No.: WO2011/090194
PCT Pub. Date: Jul. 28, 2011

(65) Prior Publication Data
US 2012/0277649 A1    Nov. 1, 2012

(30) Foreign Application Priority Data
Jan. 22, 2010    (JP) .................. 2010-012512

(51) Int. Cl.
*A61F 13/00*    (2006.01)
*A41D 13/06*    (2006.01)
(Continued)

(52) U.S. Cl.
CPC ............ *A41D 13/065* (2013.01); *A61F 2/68* (2013.01); *A61F 5/0109* (2013.01); *A61F 13/00* (2013.01); *A61F 13/08* (2013.01); *A61F 13/14* (2013.01); *A61F 2002/7645* (2013.01)

(58) Field of Classification Search
CPC ....... A61F 13/00; A61F 13/14; A61F 13/061; A61F 13/08; A61F 5/0585; A61F 5/0111; A61F 5/0113; A61F 5/0118; A61F 5/0123; A61F 5/0109; A61F 2/68; A61F 2002/7645; A41D 13/065

USPC ........ 602/5, 23, 26, 60–64, 20; 2/455, 22, 24; D24/190–192
See application file for complete search history.

(56) References Cited

U.S. PATENT DOCUMENTS 3,084,685 A *  4/1963  Lewis ............................ 602/26
4,492,227 A    1/1985  Senn et al.
(Continued)

FOREIGN PATENT DOCUMENTS

JP    1-65021       4/1989
JP    03-070558     3/1991
(Continued)

OTHER PUBLICATIONS

International Search Report of International Application No. PCT/JP2011/051220 dated Mar. 1, 2011.
(Continued)

Primary Examiner — Kim M Lewis
(74) Attorney, Agent, or Firm — Dingman, McInnes & McLane LLP (57) ABSTRACT A knee joint supporter which can improve the stability of the knee joint, reduce the wearer's fatigue and reduce the load on the patellar tendon includes a first anchor section formed by wrapping one end of a tubular knitted fabric around the wearer's thigh to tighten it with the fabric, a second anchor section formed by wrapping the other end of the fabric around the wearer's lower thigh to tighten it with the fabric, and a substantially U-shaped knitted supporting section joined to the first anchor section, covering the wearer's patella region and thus supporting the wearer's patella. In the circumferential direction of the fabric, the stretch resistance of the two anchor parts are larger than the stretch resistance of a base fabric section. In the length width direction of the fabric, the stretch resistance of the supporting section is larger than the stretch resistance of the base fabric section.

14 Claims, 8 Drawing Sheets (51) Int. Cl.
*A61F 13/14* (2006.01)
*A61F 13/08* (2006.01)
*A61F 2/68* (2006.01)
*A61F 5/01* (2006.01)
*A61F 2/76* (2006.01)

(56) References Cited

U.S. PATENT DOCUMENTS 5,154,690 A 10/1992 Shiono
6,063,048 A 5/2000 Bodenschatz et al.
6,149,616 A 11/2000 Szlema et al.

FOREIGN PATENT DOCUMENTS

JP 2007054126 3/2007
JP 2008106404 A 5/2008

OTHER PUBLICATIONS

European Search Report of European Application No. 11734800.3 Dated Dec. 10, 2013.

* cited by examiner

KNEE JOINT SUPPORTER

TECHNICAL FIELD

The present invention relates to a knee joint supporter which can support wearer's daily motion, and particularly, to a knee joint supporter having a taping function of improving the stability of the knee joint, thereby reducing the fatigue of a wearer and also reducing a load on the patellar tendon.

BACKGROUND ART

The lowering of the muscular power (in particular, the quadriceps femoris muscle) of the knee joint makes daily motion such as walking, rising from a chair, seating, or going up and down stairs difficult.

Further, in a state where the muscular power is lowered or a state of relative lack of the muscular power (a case where a muscle is overloaded in the balance between operation action and muscular power), support is performed by a passive element (the tendon, the ligament, or the like), and abrasion of the articular cartilage or inflammation of the tendon or the ligament is caused by repeating the support by the passive element. In particular, pain of the patella (the periphery of the kneecap) is also the case of a patellar tendinitis, so that support of the patella is needed.

Regarding this, a supporter in the related art has a tubular main body made of a stretchable material and a supporting part integrally provided at the main body and made of a lower stretchable material than that of the main body. The supporting part includes an anchor section which fixes the main body to the human body, an engagement section which is engaged with the knee, and a connection section which connects the anchor section and the engagement section to each other, thereby suppressing the displacement of the knee to the body trunk side with respect to the limb axis (refer to PTL 1, for example).

CITATION LIST

Patent Literature

[PTL 1] JP-A-2008-106404

SUMMARY OF INVENTION

Technical Problem

The supporter in the related art is a supporter which can effectively prevent injury to the knee due to excessive medial rotation or valgus and protect the knee, and the connection section is provided so as to connect the engagement section and the anchor section in a linear fashion along the lateral surface of the leg. However, the connection section is not provided at the medial surface of the leg. For this reason, the supporter in the related art lacks the balance between the pressing forces by the connection section which are applied to the lateral surface and the medial surface of the leg, does not improve the stability of the knee joint, and does not reduce the fatigue of a wearer.

In particular, in the supporter in the related art, since the supporting part (the anchor section, the engagement section, and the connection section) made of a lower stretchable material than that of the main body is lined and sewn to the main body, after the tubular main body is configured, a process of sewing the supporting part is required, so that there is a problem in that the manufacturing process is complicated.

Further, since the supporter in the related art does not provide a strong pressing force toward the lateral surface from the medial surface with respect to the knee of a wearer, in a case where the knee receives an external force from the lateral surface side of the leg, a repulsive force toward the lateral surface from the medial surface of the knee region, which reduces the external force, is not obtained, so that there is a problem in that the supporter is not sufficient to suppress damage to the medial collateral ligament.

The present invention has been made to solve the problems as described above and has an object to provide a knee joint supporter which improves the stability of the knee joint, thereby being able to reduce the fatigue of a wearer and also reduce a load on the patellar tendon.

Solution to Problem

A knee joint supporter according to the invention is a knee joint supporter which is made of a tubular knitted fabric that is knitted in circular knitting, and comes into close contact with the body surface of a wearer, thereby assisting a knee joint, and includes: a first anchor section which is knitted to go around one end of the tubular knitted fabric and makes the tubular knitted fabric be tightened on the thigh of the wearer; a second anchor section which is knitted to go around the other end of the tubular knitted fabric and makes the tubular knitted fabric tightened on the lower thigh of the wearer; and a supporting section which is knitted in an approximate U-shape that is connected to the first anchor section and surrounds a section corresponding to the patella of the wearer, and supports the patella of the wearer, wherein the stretch resistances of the first anchor section and the second anchor section in a circumferential direction of the tubular knitted fabric are larger than the stretch resistance of a base fabric section in the circumferential direction of the tubular knitted fabric, and the stretch resistance of the supporting section in a length direction of the tubular knitted fabric is larger than the stretch resistance of the base fabric section in the length direction of the tubular knitted fabric.

Advantageous Effects of Invention

In the knee joint supporter according to the invention, by holding the knee region by the supporting section, the knee of a wearer who wears the knee joint supporter does not shake from side to side more than necessary and stability can be secured.

BRIEF DESCRIPTION OF DRAWINGS

[FIG. 1]

[FIG. 2]

[FIG. 3]

[FIG. 4]

[FIG. 5]

[FIG. 6]

[FIG. 7]

[FIG. 8]

DESCRIPTION OF EMBODIMENTS (First Embodiment of the Invention)

In FIGS. 1, 2, and 6 or 7, a knee joint supporter 10 is made of a tubular knitted fabric which is knitted in circular knitting by a hosiery knitting machine (for example, a type of knitting machine (number of needles: 256) manufactured by Lonati Co.), and is a supporter which comes into close contact with the body surface of a wearer, thereby assisting the knee joint of the wearer.

The knee joint supporter 10 has a desired functionality such as a taping function by performing different knitting with respect to a base fabric section 1 that is a stretchable knitted fabric which is knitted in a plain stitch, a rib stitch, a tuck stitch, a float stitch, a pile stitch, or the like by using an upper thread, an under thread, and a rubber thread as knitting yarn.

In addition, the base fabric section 1 related to this embodiment is a knitted fabric which is knitted in a rib stitch (hereinafter referred to as a rib stitch knitted fabric).

Further, the knee joint supporter 10 has a first anchor section 2 which is knitted to go around one end (an upper end 10a) of the tubular knitted fabric and makes the knee joint supporter 10 be tightened on the thigh of a wearer, and a second anchor section 3 which is knitted to go around the other end (a lower end 10b) of the tubular knitted fabric and makes the knee joint supporter 10 be tightened on the lower thigh of the wearer.

The first anchor section 2 and the second anchor section 3 are knitted such that the stretch resistances thereof in a circumferential direction H of the knee joint supporter 10 (the tubular knitted fabric) are larger than the stretch resistance of the base fabric section 1 in the circumferential direction H of the knee joint supporter 10. That is, when tension in a case where certain elongation has been imparted from a state where elongation is not imparted to a material is set to be F, the tension of the base fabric section 1 in the circumferential direction H of the knee joint supporter 10 is set to be $F_{H1}$, the tension of the first anchor section 2 in the circumferential direction H of the knee joint supporter 10 is set to be $F_{H2}$, and the tension of the second anchor section 3 in the circumferential direction H of the knee joint supporter 10 is set to be $F_{H3}$, the first anchor section 2 and the second anchor section 3 have such a magnitude relation of $F_{H2} \approx F_{H3} > F_{H1}$ that they have strong tightening forces in the circumferential direction H of the knee joint supporter 10, compared to the base fabric section 1.

Specifically, by making each of the first anchor section 2 and the second anchor section 3 be a knitted fabric knitted in a moss stitch (hereinafter referred to as a moss stitch knitted fabric), it is possible to make the stretch resistance thereof in the circumferential direction H of the knee joint supporter 10 large with respect to the base fabric section 1 that is the rib stitch knitted fabric.

In addition, the moss stitch knitted fabric is a knitted fabric in which a plain stitch and a tuck (a structure in which no loop protrudes over a certain course and plural loops protrude over the subsequent course) appear alternately or for every few courses in the course direction and the wale direction. For this reason, in the first anchor section 2 and the second anchor section 3, the plain stitch and the tuck are used in combination, whereby it is possible to make protuberances or openwork stitches on the surface of a knitted fabric and a mesh pattern such as a moss appears.

In this manner, the first anchor section 2 is knitted to surround the thigh of a wearer, and the stretch resistance of the first anchor section 2 in the circumferential direction H of the knee joint supporter 10 is Larger than the stretch resistance of the base fabric section 1 in the circumferential direction H of the knee joint supporter 10, whereby it is possible to fix the knee joint supporter 10 to the thigh of a wearer and suppress slipping-off of the upper end 10a of the knee joint supporter 10 at the time of the flexion of the knee joint. Further, the first anchor section 2 is connected to a supporting section 4 (described later), thereby also functioning as an anchor of the supporting section 4.

Further, the second anchor section 3 is knitted to surround the lower thigh of a wearer, and the stretch resistance of the second anchor section 3 in the circumferential direction H of the knee joint supporter 10 is larger than the stretch resistance of the base fabric section 1 in the circumferential direction H of the knee joint supporter 10, whereby it is possible to fix the knee joint supporter 10 to the lower thigh of a wearer and suppress slipping-off of the lower end 10b of the knee joint supporter 10 at the time of the flexion of the knee joint.

In addition, if tightening forces on the thigh and the lower thigh of a wearer by the first anchor section and the second anchor section 3 are too strong, constriction of blood flow in the thigh and the lower thigh occurs, thereby causing a feeling of discomfort to the wearer. In particular, the feeling of discomfort is remarkable in the thigh, compared to the lower thigh.

For this reason, in the knee joint supporter 10 related to this embodiment, the feeling of discomfort which is imparted to a wearer is alleviated by widening the area of the first anchor section 2 which comes into contact with the body surface of the wearer, with respect to the second anchor section 3, thereby dispersing pressure which is applied to the body surface by the first anchor section 2, and also adjusting density in a portion of the first anchor section 2 (for example, to make a tightening force thereof small by about 10% with respect to the second anchor section 3). That is, it is preferable that the knee joint supporter 10 related to this embodiment have a magnitude relation of $F_{H3} > F_{H2} > F_{H1}$ so as to have a moderate tightening force in the circumferential direction H of the knee joint supporter 10.

The supporting section 4 is knitted in an approximate U-shape which is connected to the first anchor section 2 and surrounds a section (a patella corresponding section 5 (described later)) corresponding to the patella of a wearer, and supports the patella of the wearer. In particular, the supporting section 4 is connected to the second anchor section 3 and extends between the first anchor section 2 and the second anchor section 3 to correspond to the medial collateral ligament and the lateral collateral ligament of a wearer. That is, the supporting section 4 is locked at the first anchor section 2 on the thigh side of a wearer and locked at the second anchor section 3 on the lower thigh side of the wearer.

In addition, in a case where the supporting section is not connected to the second anchor section 3, the base fabric section 1 having stretching properties is present between the supporting section 4 and the second anchor section 3, so that there is a fear that a position shift of the supporting section 4 with respect to the patella of a wearer may occur. For this reason, the supporting section 4 is connected to the second anchor section 3, whereby stable wear becomes possible.

Figure 7A:
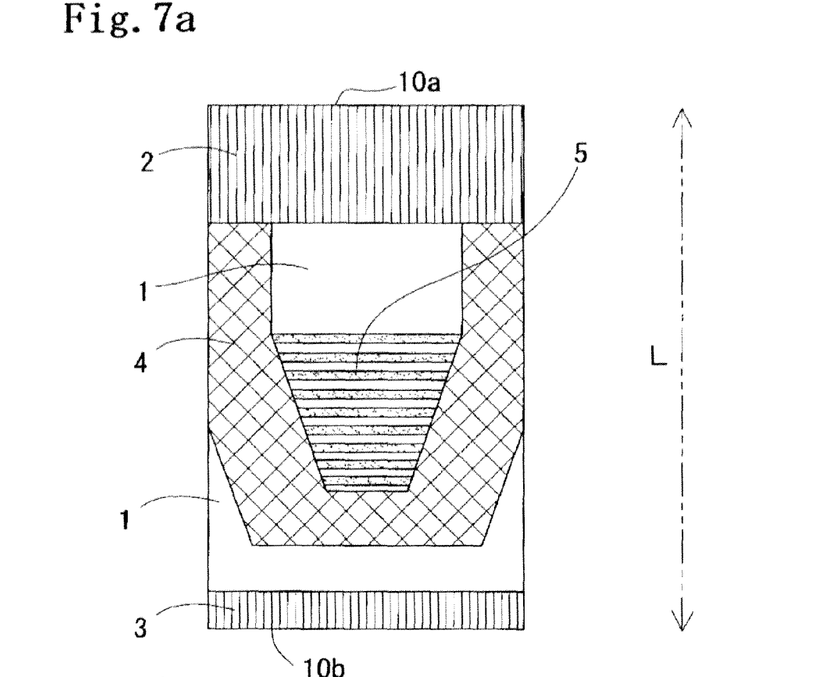
FIG. 7(a) is a front view showing the schematic configuration of another knee joint supporter related to the first embodiment.

Further, the knee joint supporter 10 related to this embodiment can also be configured such that the base fabric section 1 is continuously interposed between the supporting section 4 and the second anchor section 3, as shown in FIG. 7(a). According this configuration, due to the high stretching properties of the base fabric section 1, the locking force of the supporting section 4 by the second anchor section 3 is weakened, so that an action of supporting the patella of a wearer from the lower thigh side by the supporting section 4 can be reliably performed.

Further, it is preferable that the supporting section 4 be formed such that the stretch resistance in the length direction of the supporting section 4 becomes large compared to the stretch resistance in the width direction of the supporting section 4. However, it is difficult to knit a knitted fabric with a difference in the stretch resistance imparted thereto, by circular knitting. Therefore, in this embodiment, the supporting section 4 is formed in which the stretch resistance thereof in a length direction L of the knee joint supporter 10 is large compared to the stretch resistance thereof in the circumferential direction H of the knee joint supporter 10 so as to approximate to a knitted fabric with a difference in the stretch resistance imparted thereto.

Further, the supporting section 4 is knitted such that the stretch resistance thereof in the length direction L of the knee joint supporter 10 is larger than the stretch resistance of the base fabric section 1 in the length direction L of the knee joint supporter 10. That is, when the tension of the base fabric section 1 in the length direction L of the knee joint supporter 10 is set to be $F_{L1}$ and the tension of the supporting section 4 in the length direction L of the knee joint supporter 10 is set to be $F_{L4}$, the supporting section 4 has such a magnitude relation of $F_{L4} > F_{L1}$ that it has a strong tightening force in the length direction L of the knee joint supporter 10, compared to the base fabric section 1.

Specifically, by making the supporting section 4 be a knitted fabric in which a tuck stitch and a plating stitch are used in combination (hereinafter referred to as a tuck stitch-plating stitch knitted fabric), it is possible to make the stretch resistance thereof in the length direction L of the knee joint supporter 10 large with respect to the base fabric section 1 that is the rib stitch knitted fabric.

In addition, a tuck stitch knitted fabric is a knitted fabric in which a certain loop is not made temporarily when knitting the fabric and loops are made together when knitting the next course. In addition, in this embodiment, in consideration of a balance with density, the number of times to tuck is set to be twice. However, the number of times is not limited thereto.

Further, in the tuck stitch-plating stitch knitted fabric, expansion and contraction of the supporting section 4 in the length direction L of the knee joint supporter 10 is moderately suppressed by additionally feeding another knitting yarn (for example, woolly nylon yarn) in addition to the ground knitting yarn of the tuck stitch, and another knitting yarn is cut at the boundary between the supporting section 4 and the base fabric section 1 (a cut boss).

In this manner, the supporting section 4 is knitted in an approximate U-shape which is connected to the first anchor section 2 and surrounds a section corresponding to the patella of a wearer, and the stretch resistance thereof in the length direction L of the knee joint supporter 10 is larger than the stretch resistance of the base fabric section 1 in the length direction L of the knee joint supporter 10, whereby the following operation and effects are obtained.

The supporting section 4 supports the patella of a wearer toward the thigh side from the lower thigh side and also supports the medial collateral ligament, thereby being able to make the movement of the quadriceps femoris muscle smooth and suppress the shake from side to side of the knee. That is, the supporting section 4 supports the patella of a wearer from the lower thigh side within an approximate U-shape, thereby being able to act like a splint which is integrated with the movement of the quadriceps femoris muscle and suppress the shake from side to side of the knee.

Further, special function knitting (the tuck stitch-plating stitch knitted fabric) in the supporting section 4 is connected to the moss stitch knitted fabrics in the first anchor section 2 and the second anchor section 3 and prevents a position shift of the supporting section 4 with respect to the patella of a wearer, so that it is possible to fix the supporting section 4 to an appropriate position.

Further, the supporting section 4 imparts a strong pressing force toward a lateral surface from a medial surface with respect to the knee of a wearer who wears the knee joint supporter 10, whereby in a case where the knee receives an external force from the lateral surface side of the knee joint supporter 10, the supporting section 4 can generate a repulsive force toward the lateral surface from the medial surface, which reduces the external force, so that the knee does not get into the inside by the external force and damage to the medial collateral ligament can be suppressed.

Further, the supporting section 4 supports the thigh and the lateral surface of the knee of a wearer who wears the knee joint supporter 10, thereby being able to balance with a pressing force which is applied to the medial surface by the supporting section 4, so that the wearer can maintain a stable standing state. In particular, by holding the patella corresponding section 5 (described later) by the supporting section 4, the knee of a wearer who wears the knee joint supporter 10 does not shake from side to side more than necessary and stability can be secured.

Figure 6A:
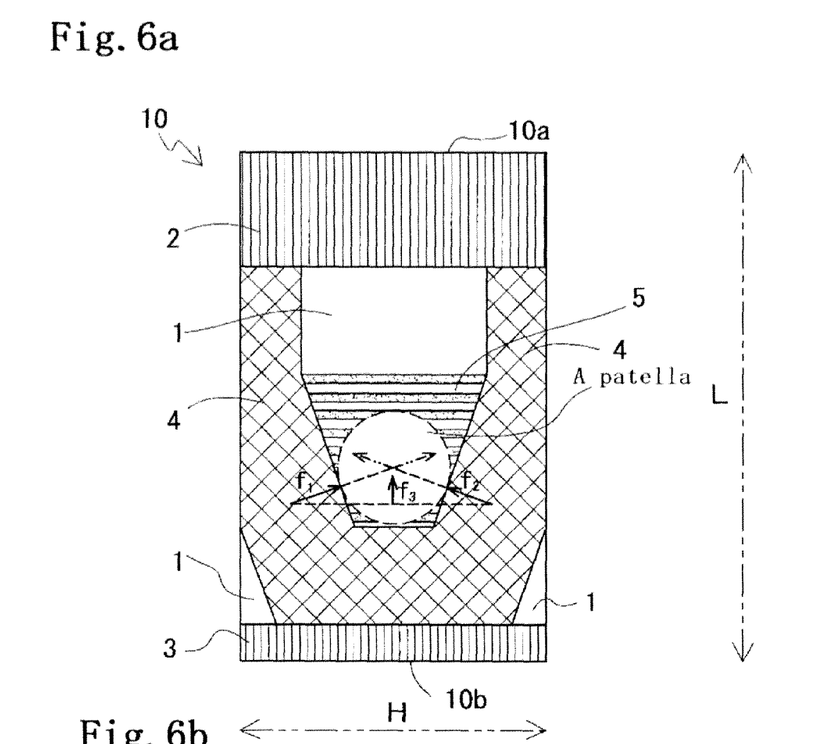
FIG. 6(a) is an explanatory diagram for describing the operation and effects by a supporting section of the knee joint supporter shown in FIG. 1(a)

In particular, the supporting section 4 has a shape in which the inner sides in the approximate U-shape have tapers widening from the second anchor section 3 side to the first anchor section 2 side, whereby a resultant force $f_3$ of forces $f_1$ and $f_2$ which are respectively directed toward the center of the patella approximately vertically from the inner sides of the tapers on the left and right sides with respect to the patella of a wearer acts vertically upward on the patella, as shown in FIG. 6(a), so that it is possible to reliably lift vertically upward the patella of the wearer in a stable state where no lateral shake is present.

Figure 6B:
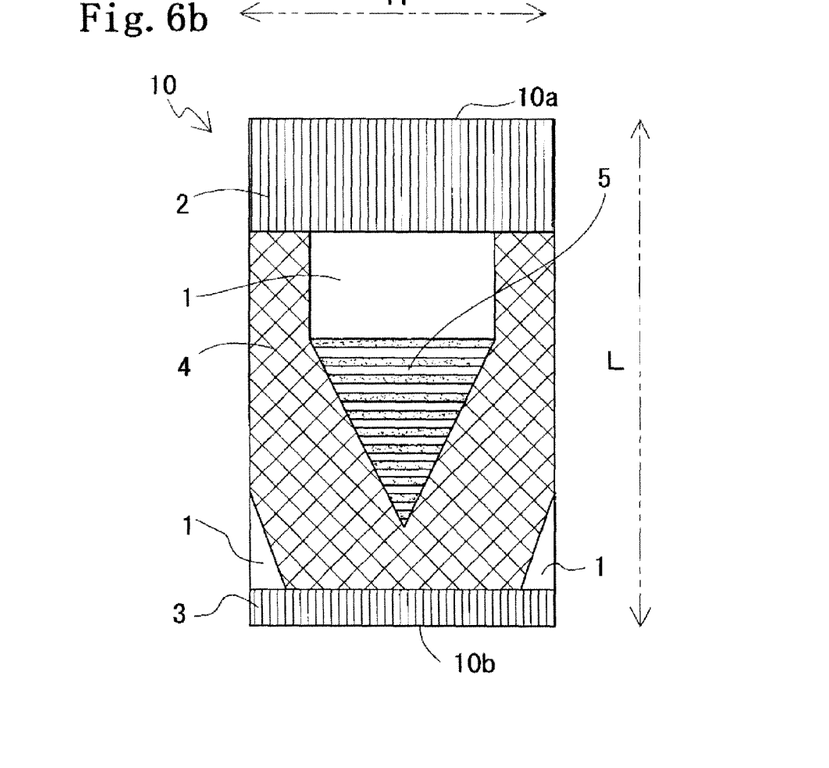
FIG. 6(b) is a front view showing the schematic configuration of another knee joint supporter related to the first embodiment.

In addition, as long as the supporting section 4 has a shape in which the inner sides in the approximate U-shape have tapers widening from the second anchor section 3 side to the first anchor section 2 side, the supporting section 4 may also be knitted in an approximate V-shape in which ends on one side of the left and right tapers conform to each other, as shown in FIG. 6(b), for example.

The patella corresponding section 5 is a section which is knitted on the front face side of the knee joint supporter 10 and corresponds to the patella of a wearer, and in this embodiment, an area surrounded by the supporting section 4 and the first anchor section 2 is configured by the patella corresponding section 5 of an approximately trapezoidal shape and the base fabric section 1 of an approximately rectangular shape.

The patella corresponding section 5 is knitted such that the stretch resistance thereof in the length direction L of the knee joint supporter 10 is smaller than the stretch resistance of the base fabric section 1 in the length direction L of the knee joint supporter 10. That is, when the tension of the patella corresponding section 5 in the length direction L of the knee joint supporter 10 is set to be $F_{L5}$, the patella corresponding section 5 has such a magnitude relation of $F_{L1} > F_{L5}$ that it has a weak tightening force in the length direction L of the knee joint supporter 10, compared to the base fabric section 1.

Specifically, by making the patella corresponding section 5 be a knitted fabric knitted in a mesh stitch that is a knitting structure having good air permeability (hereinafter referred to as a mesh stitch knitted fabric), it is possible to make the stretch resistance thereof in the length direction L of the knee joint supporter 10 small with respect to the base fabric section 1 that is the rib stitch knitted fabric.

In addition, the mesh stitch knitted fabric is a knitted fabric in which a certain loop is not made temporarily when knitting the fabric and loops are made together when knitting the next course and which stretches well with knitting in the form of a mesh. In particular, the patella corresponding section 5 related to this embodiment is a knitted fabric in which a mesh stitch knitted fabric (a plain stitch knitted fabric composed of an under thread and a rubber thread without feeding an upper thread) and a plain stitch knitted fabric (a plain stitch knitted fabric composed of an upper thread, an under thread, and a rubber thread), which extend in the circumferential direction H of the knee joint supporter 10, are alternately arranged in parallel (hereinafter referred to as a bellows knitted fabric).

In the bellows knitted fabric, since the surface of the knee joint supporter 10 is nearly flat, but the thickness of the mesh stitch knitted fabric is thin with respect to the plain stitch knitted fabric, the part of the mesh stitch knitted fabric becomes a concave portion, so that concavity and convexity are created on the rear surface of the knee joint supporter 10. For this reason, the bellows knitted fabric is a knitted fabric having high stretching properties, because frictional resistance between the knee of a wearer and the patella corresponding section 5 is small due to a narrow contact area with the body surface of the wearer and frictional resistance between adjacent threads is also small due to the large loop of the mesh stitch knitted fabric.

In this manner, the patella corresponding section 5 corresponds to the patella of a wearer, and the stretch resistance thereof in the length direction L of the knee joint supporter 10 is smaller than the stretch resistance of the base fabric section 1 in the length direction L of the knee joint supporter 10, whereby forces associated with expansion and contraction of the skin of a wearer in the bending and stretching motion or the rotation motion of the knee joint can be absorbed by a high stretch function. In particular, the patella corresponding section 5 can grip the kneecap of a wearer at the time of the flexion of the knee joint due to the bellows knitted fabric having high stretching properties, and prevents a position shift in any direction of the knee joint supporter 10, so that it is possible to improve the operation and effects by the supporting section 4 described above.

A popliteal fossa contact section 6 is a section which is knitted at a position facing the patella corresponding section 5 on the rear face side of the knee joint supporter 10 and comes into contact with the popliteal fossa of a wearer, and in this embodiment, the popliteal fossa contact section 6 is an approximately trapezoidal knitted fabric.

The popliteal fossa contact section 6 is knitted such that the stretch resistance thereof in the length direction L of the knee joint supporter 10 is smaller than the stretch resistance of the base fabric section 1 in the length direction L of the knee joint supporter 10. That is, when the tension of the popliteal fossa contact section 6 in the length direction L of the knee joint supporter 10 is set to be $F_{L6}$, the popliteal fossa contact section 6 has such a magnitude relation of $F_{L1} > F_{L6}$ that it has a weak tightening force in the length direction L of the knee joint supporter 10, compared to the base fabric section 1.

Specifically, by making the popliteal fossa contact section 6 be a mesh stitch knitted fabric, it is possible to make the stretch resistance thereof in the length direction L of the knee joint supporter 10 small with respect to the base fabric section 1 that is the rib stitch knitted fabric. In particular, the popliteal fossa contact section 6 related to this embodiment is a knitted fabric (a bellows knitted fabric) in which a mesh stitch knitted fabric (a plain stitch knitted fabric composed of an under thread and a rubber thread without feeding an upper thread) and a plain stitch knitted fabric (a plain stitch knitted fabric composed of an upper thread, an under thread, and a rubber thread), which extend in the circumferential direction H of the knee joint supporter 10, are alternately arranged in parallel.

In this manner, the popliteal fossa contact section 6 is a section which comes into contact with the popliteal fossa of a wearer, and the stretch resistance thereof in the length direction L of the knee joint supporter 10 is smaller than the stretch resistance of the base fabric section 1 in the length direction L of the knee joint supporter 10, whereby the knee joint supporter 10 in close contact with the body surface of a wearer can be prevented from being lifted from the body surface. In particular, the popliteal fossa contact section 6 suppresses occurrence of wrinkles in a bent portion of the knee joint supporter 10 at the time of the flexion of the knee joint, due to the bellows knitted fabric having high stretching properties, thereby being able to prevent incidence of pain due to pinching the skin of a wearer between wrinkles, or the like.

In addition, in the knee joint supporter 10 related to this embodiment, due to the knitted fabric of each site described above, the stretch resistance of the supporting section 4 in the length direction L of the knee joint supporter 10 is larger than the stretch resistance of the second anchor section 3 in the length direction L of the knee joint supporter 10. Further, the stretch resistance of the second anchor section 3 in the length direction L of the knee joint supporter 10 is larger than the stretch resistance of the first anchor section 2 in the length direction L of the knee joint supporter 10. Further, the stretch resistance of the first anchor section 2 in the length direction L of the knee joint supporter 10 is larger than the stretch resistance of the base fabric section 1 in the length direction L of the knee joint supporter 10.

Therefore, the knee joint supporter 10 related to this embodiment satisfies a magnitude relation shown by the following expression (1) in the tension F in the length direction L of the knee joint supporter 10. However, in the following expression (1), $F_{L2}$ is the tension of the first anchor section 2 in the length direction L of the knee joint supporter 10, and $F_{L3}$ is the tension of the second anchor section 3 in the length direction L of the knee joint supporter 10.

[Expression 1]

$$F_{L4} > F_{L3} > F_{L2} > F_{L1} > F_{L5} \approx F_{L6} \quad (1)$$

In addition, in this embodiment, as the ground knitting yarn which is used in the plain stitch, the rib stitch, the moss stitch, the tuck stitch, and the mesh stitch, an upper thread which is nylon yarn having thickness of 70 deniers and is composed of two pieces of knitting yarn, an under thread which is nylon yarn having a thickness of 30 deniers and is composed of two pieces of knitting yarn, and a rubber thread which is covering yarn (DCY: double covered yarn) in which two pieces of nylon winding yarn each having a thickness of 40 deniers are wound around polyurethane core yarn having a thickness of 260 deniers are used. However, the threads are not limited to these materials.

For example, as the upper thread, it is preferable to select a natural fiber such as cotton, wool (cashmere, lamb, Angora, or the like), silk, or hemp, a chemical fiber such as acrylic, a material having a sweat absorbing, quick-drying, or body temperature adjusting function, or the like according to the cost of the knee joint supporter 10 or the needs of a wearer. Further, as the under thread, it is preferable to select an ester, FTY (filament twisted yarn), or an antibacterial, deodorant, or odor eliminating material according to the cost of the knee joint supporter 10 or the needs of a wearer.

Further, the woolly nylon yarn (pattern yarn) in the tuck stitch-plating stitch knitted fabric (the supporting section 4) is composed of two pieces of knitting yarn each having a thickness of 100 deniers.

Figure 7B:
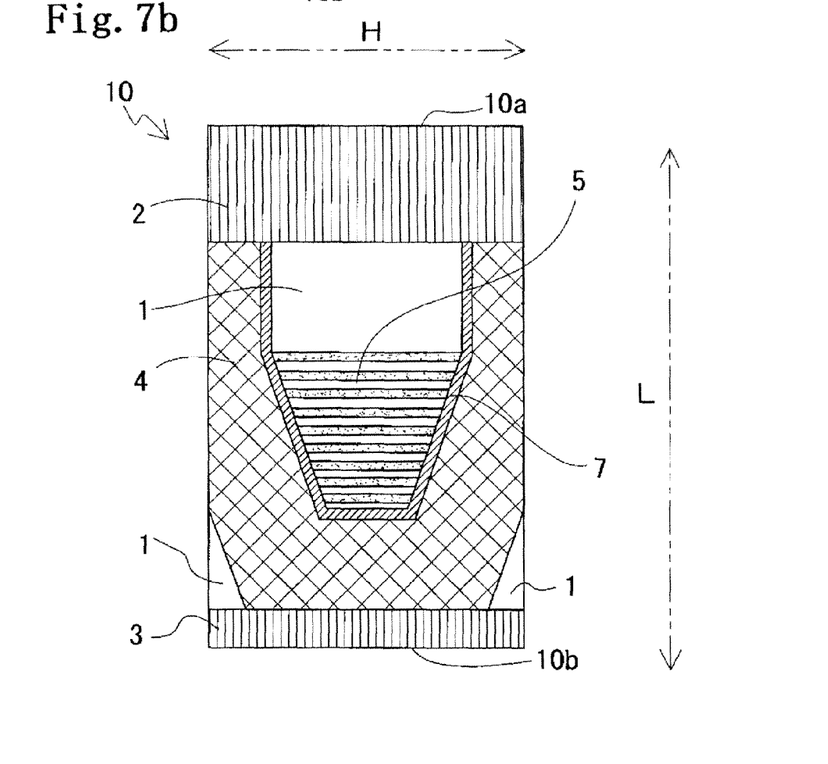
FIG. 7(b) is a front view showing the schematic configuration of still another knee joint supporter related to the first embodiment.

In addition, a knitted fabric of the boundary between the patella corresponding section 5 related to this embodiment and the base fabric section 1 adjacent to the patella corresponding section 5 and the supporting section 4 is knitted such that an upper thread which is used in the patella corresponding section 5 or the base fabric section 1 and an upper thread which is used in the supporting section 4 are continuous without overlapping each other, as shown in FIG. 1(*a*). However, as shown in FIG. 7(*b*), a knitted fabric 7 of the boundary between the patella corresponding section 5 and the base fabric section 1 adjacent to the patella corresponding section 5 (the base fabric section 1 adjacent to the patella corresponding section 5 is excluded, as necessary) and the supporting section 4 is knitted by overlapping an upper thread which is used in the patella corresponding section 5 or the base fabric section 1 and an upper thread which is used in the supporting section 4 and using the upper threads along with a common under thread which is used in the patella corresponding section 5 or the base fabric section 1 and the supporting section 4. In particular, in the knitting shown in FIG. 7(*b*), since the knitted fabric reinforces the boundary between the patella corresponding section in which expansion and contraction by the flexion and extension of the knee joint are largest and a load is largest, and the base fabric section 1 adjacent to the patella corresponding section 5 and the supporting section 4, a break of the boundary, loosening of the knitting yarn, or the like can be prevented.

Figure 1A:
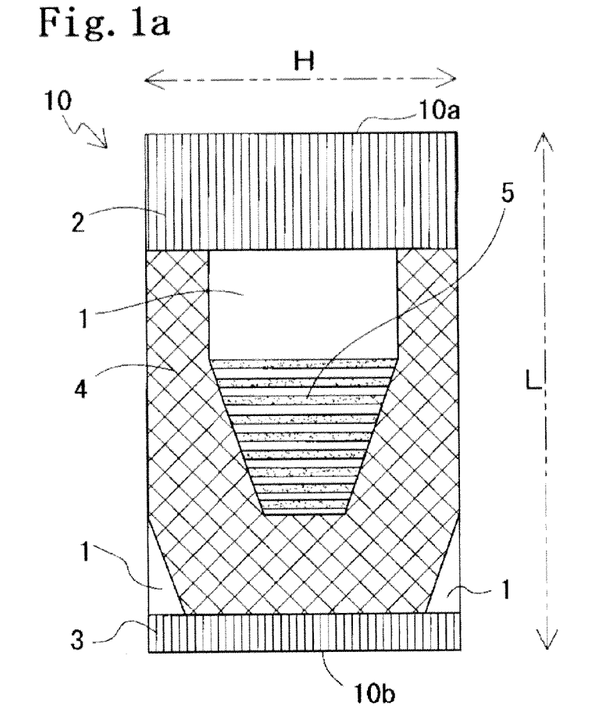
FIG. 1(a) is a front view showing the schematic configuration of a knee joint supporter related to the first embodiment.
Figure 1B:
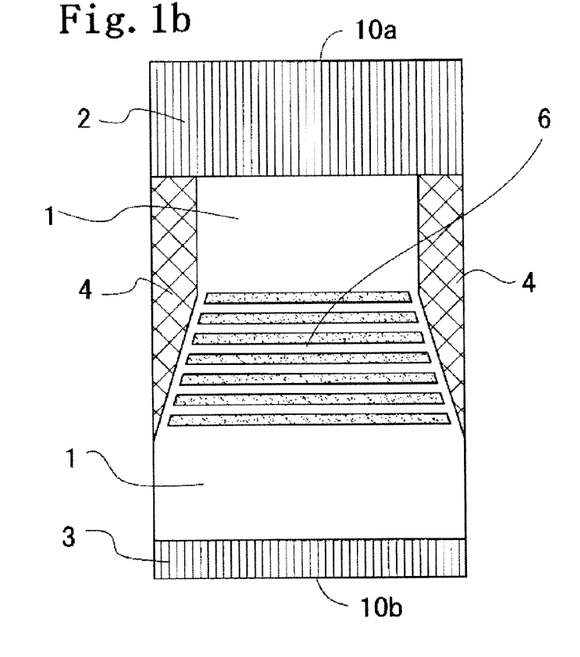
FIG. 1(b) is a back view of the knee joint supporter shown in FIG. 1(a)
Figure 1C:
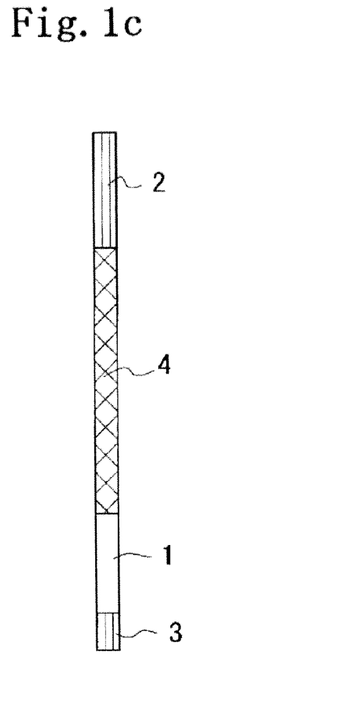
FIG. 1(c) is a left side view and right side view of the knee joint supporter shown in FIG. 1(a)
Figure 1D:
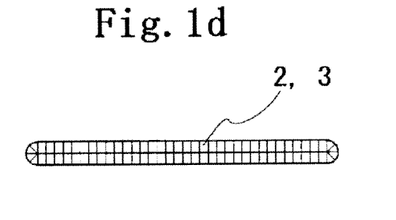
FIG. 1(d) is a plan view and bottom view of the knee supporter shown in FIG. 1(a).
Figure 2A:
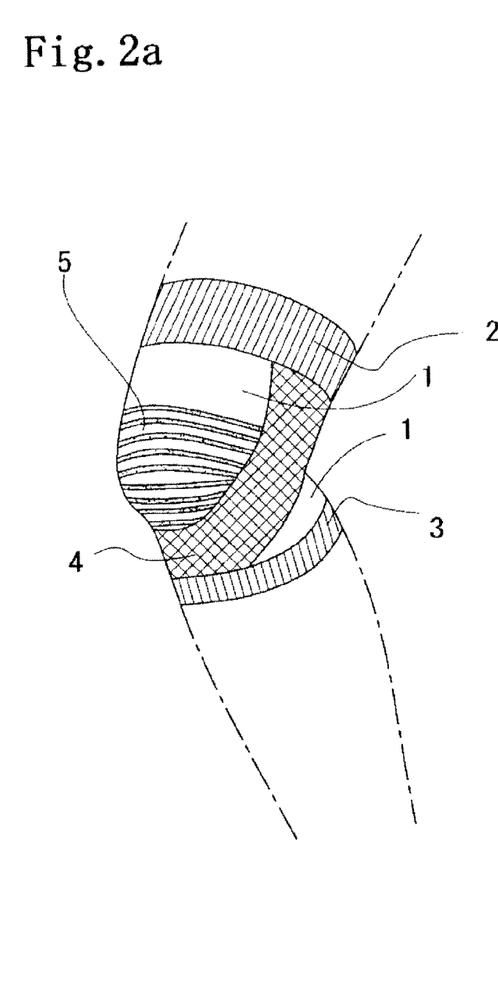
FIG. 2(a) is a perspective view showing a wearing state of the knee joint supporter shown in FIG. 1.
Figure 2B:
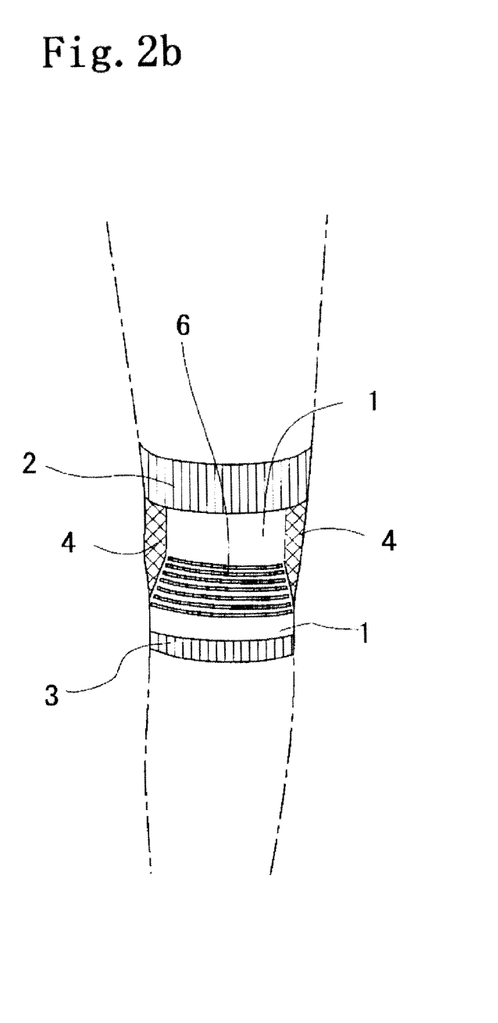
FIG. 2(b) is a back view showing a wearing state of the knee joint supporter shown in FIG. 1.
Figure 3A:
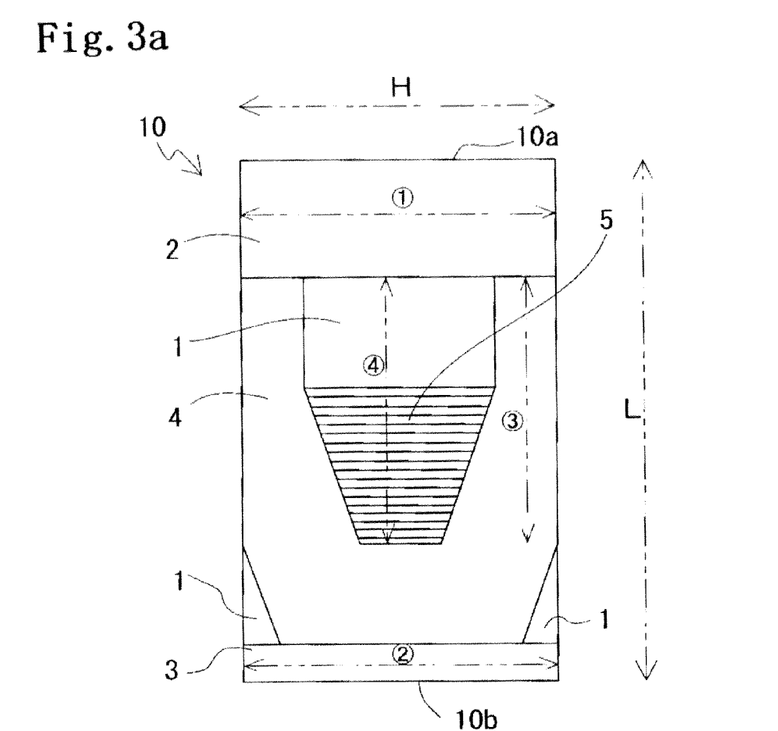
FIG. 3(a) is an explanatory diagram for describing sites for measuring an elongation rate in the knee joint supporter shown in FIG. 1(a)
Figure 3B:
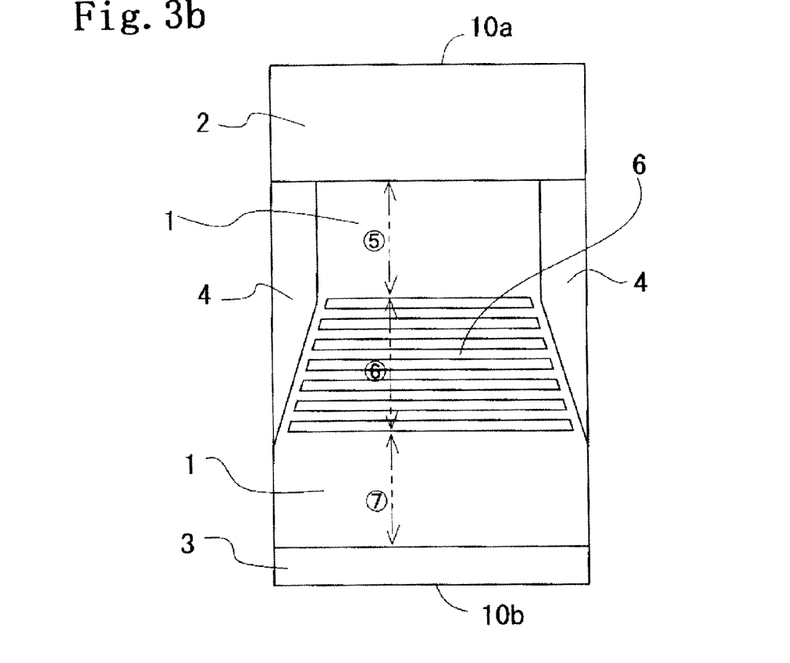
FIG. 3(b) is an explanatory diagram for describing sites for measuring an elongation rate in the knee joint supporter shown in FIG. 1(b).

Here, the results of measurement of an elongation rate (the percentage of a difference between a length when elongated (an elongated dimension) and the original length (the original dimension) to the original length) measured with respect to the respective site (refer to FIG. 3) of the knee joint supporter 10 made according to the above-described knitting yarn and knitted fabrics by using a stretch tester (tensile load: 4 kg) are shown in Table 1 below.

TABLE 1

| Measured site | | Original dimension [cm] | Elongated dimension [cm] | Elongation rate [%] |
|---|---|---|---|---|
| Circled number 1 | Circumferential direction H of the first anchor section 2 | 14.0 | 33.5 | 139.3 |
| Circled number 2 | Circumferential direction H of the second anchor section 3 | 13.3 | 30.5 | 129.3 |
| Circled number 3 | Length direction L of the supporting section 4 | 10.4 | 19.0 | 82.7 |
| Circled number 4 | Length direction L over the base fabric section 1 and the patella corresponding section 5 | 10.4 | 26.0 | 150.0 |
| Circled number 5 | Length direction L of the base fabric section 1 in an upper portion on the rear face side | 5.0 | 12.0 | 140.0 |
| Circled number 6 | Length direction L of the popliteal fossa contact section 6 | 5.0 | 17.0 | 240.0 |
| Circled number 7 | Length direction L of the base fabric section 1 in a lower portion on the rear face side | 5.0 | 11.0 | 120.0 |

In addition, since the elongation rate in Table 1 represents the fact that the larger the value, the more easily the knitted fabric is elongated and the tension F in the above-described expression (1) represents the fact that the larger the value, the more difficult it is for the knitted fabric to be elongated (the larger the tightening force), an inequality sign showing the magnitude relation of the elongation rate and an inequality sign showing the magnitude relation of the tension F become opposite to each other.

Next, the result of verification of the operation and effects of the knee joint supporter 10 related to this embodiment will be described.

Figure 4A:
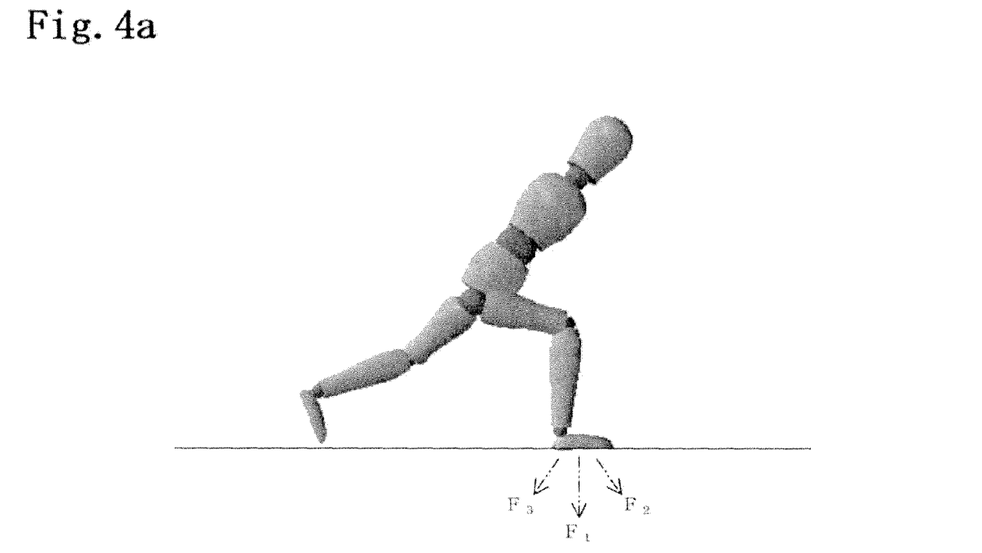
FIG. 4(a) is an explanatory diagram for describing an experimental motion of a test subject for verifying the operation and effects of the knee joint supporter shown in FIG. 1.

In the first experiment, in a case where the knee joint supporter 10 is worn on the right knee of a test subject (a 26-years-old healthy male, there is no anamnesis in four limbs) (hereinafter referred to as the time of wear) and a case where the knee joint supporter 10 is not worn (hereinafter referred to as the time of non-wear), a state where the right foot takes a step forward from an upright state (a lunge motion) and the left foot is away from a floor was maintained for 10 seconds (FIG. 4(*a*)) and the amount of work (the degree of bracing) of a knee joint moment was measured as a weighted force $F_1$ in a vertical direction shown in FIG. 4(*a*) by three-dimensional motion analysis.

Figure 4B:
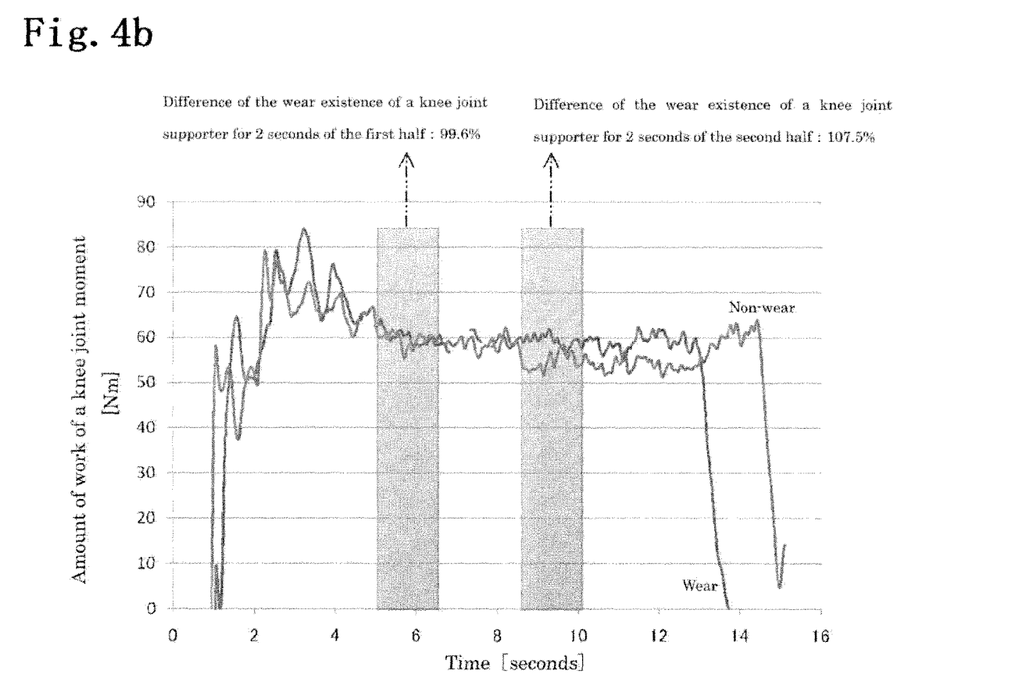
FIG. 4(b) is a graph showing the measurement results for verifying the operation and effects of the knee joint supporter shown in FIG. 1.

In addition, in the three-dimensional motion analysis, a three-dimensional motion analysis system "VICON MX" manufactured by VICON, Inc. was used. Further, as shown in FIG. 4(*b*), in a time (about 3 seconds) from the start of the measurement to a time when the left foot is separated from the floor, a weight shift from both feet to the right foot is made by a lunge motion, and until a certain amount of time has elapsed, since balance by standing on one leg cannot be maintained, a change in the amount of work of a knee joint extension moment is large. For this reason, in the verification, measurement data from a point of time (about 5 seconds) when a certain amount of time has elapsed to a time (about 13 seconds) until the left foot lands on the floor was verified.

As shown in FIG. 4(b), the amount of work of the knee joint extension moment at the time of wear is nearly constant in the vicinity of 60 Nm in a period from about 5 seconds to about 13 seconds. In contrast, it can be found that the amount of work of the knee joint extension moment at the time of non-wear is nearly constant in the vicinity of 60 Nm in a period from about 5 seconds to about 9 seconds, but becomes smaller than 60 Nm in a period from about 9 seconds to about 13 seconds. This is considered to be because at the time of non-wear of the knee joint supporter 10, due to a load on the knee joint, the same posture cannot be maintained and a staggering motion occurs (the knees be about to give way), the weighted force $F_1$ in the vertical direction in FIG. 4(a) is dispersed into weighted forces $F_2$ and $F_3$ in the front and rear oblique directions, so that the weighted force $F_1$ in the vertical direction is reduced and the amount of work (the degree of bracing) of the knee joint extension moment becomes small.

In particular, for 2 seconds of the first half, the percentage of the amount of work of the knee joint extension moment at the time of wear to the amount of work of the knee joint extension moment at the time of non-wear is 99.6%. In contrast, for 2 seconds of the second half, the percentage of the amount of work of the knee joint extension moment at the time of wear to the amount of work of the knee joint extension moment at the time of non-wear is 107.5%. This means that by wearing the knee joint supporter 10, for 2 seconds of the second half, the amount of work of the knee joint extension moment increases.

In the second experiment, in a case where the knee joint supporters 10 are worn on the right knees of three test subjects (healthy adult males, average age: 29±3.6-years-old, average height: 169.7±4.9 cm, and average weight: 64.3±11.9 kg) (the time of wear) and a case where the knee joint supporter 10 is not worn (the time of non-wear), a state where the right foot takes a step forward from an upright state (a lunge motion) and the left foot is away from a floor was maintained for 10 seconds (FIG. 4(a)).

The measurement results are the results in which the integrated value of the knee joint extension moment of each test subject for 3 seconds from 8 seconds after the start of measurement to 11 seconds to exclude a time zone (the first half and the second half) when the test subject is in an unstable state is normalized by the weight of each test subject, and are shown in Table 2 below and FIG. 5.

TABLE 2

|  | Test subject 1 (Nm/kg) | Test subject 2 (Nm/kg) | Test subject 3 (Nm/kg) | Average value (Nm/kg) |
|---|---|---|---|---|
| Non-wear | 494.4687692 | 310.81175 | 310.6487797 | 371.976433 |
| Wear | 547.1222821 | 332.3266875 | 437.1894576 | 438.8794757 |

Figure 5A:
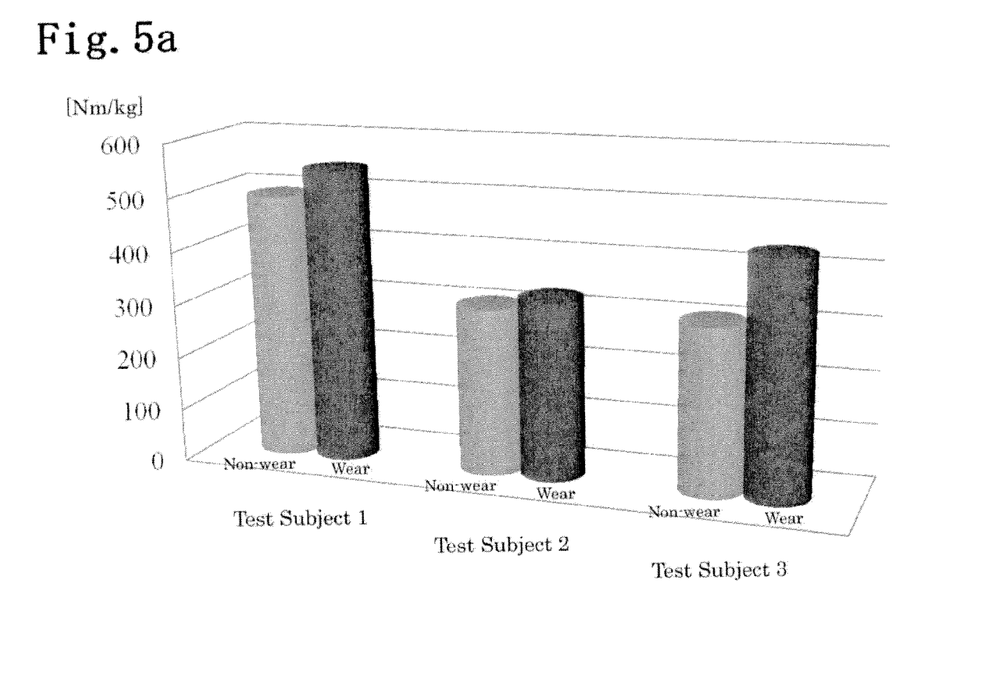
FIG. 5(a) is a graph showing the measurement results on each test subject for verifying the operation and effects of the knee joint supporter shown in FIG. 1.
Figure 5B:
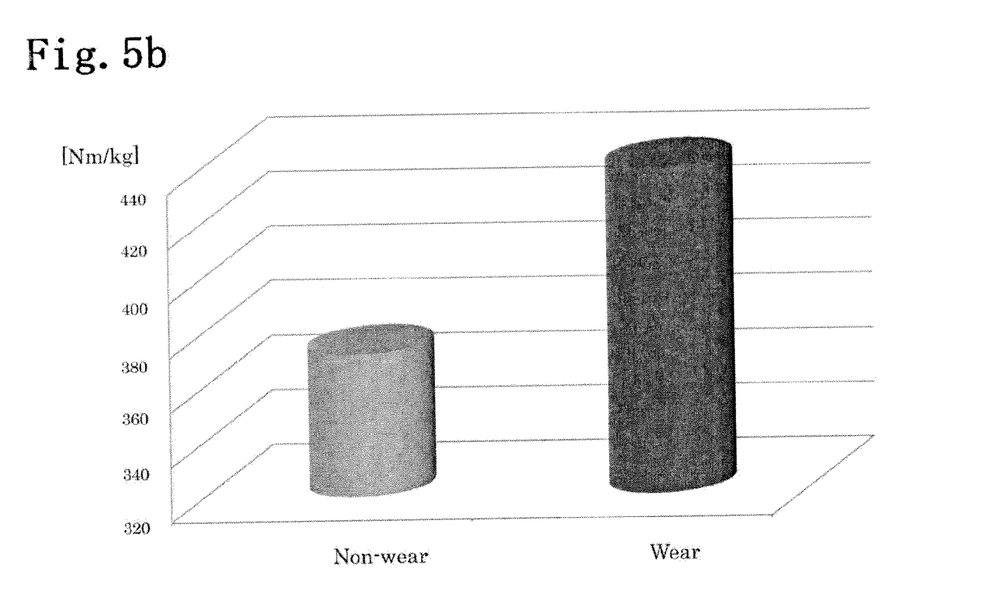
FIG. 5(b) is a graph showing the average value of the measurement results shown in FIG. 5(a).

As shown in Table 2 and FIG. 5, it can be found that in all the test subjects, at the time of wear of the knee joint supporter 10, compared to the time of non-wear, the amount of work (the degree of bracing) of the knee joint extension moment becomes large.

As described above, it can be found that the knee joint supporter 10 has the operation and effects of improving the stability of the knee joint, thereby reducing the fatigue of a wearer and also reducing a load on the patellar tendon.

(Second Embodiment of the Invention)

Figure 8A:
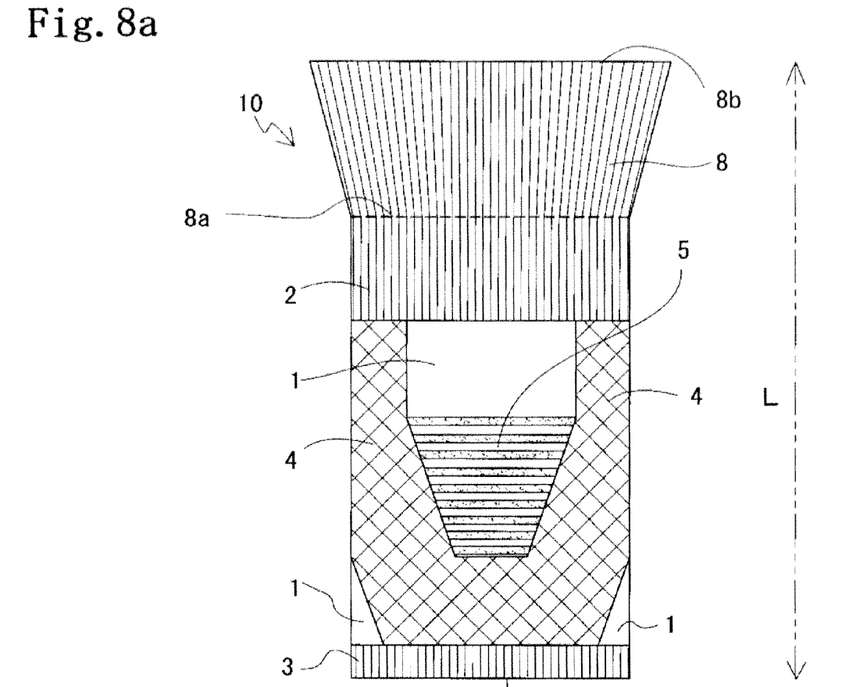
FIG. 8(a) is a front view showing the schematic configuration of a knee joint supporter related to the second embodiment.

FIG. 8(a) is a front view showing the schematic configuration of a knee joint supporter related to the second embodiment. In FIG. 8(a), the same symbol as that in FIGS. 1, 2, and 6 or 7 denotes the same or equivalent section, and explanation thereof is omitted.

In FIG. 8(a) described above, the knee joint supporter 10 related to this embodiment is configured to have, in addition to the configuration in the first embodiment described above, a curling prevention section 8 which is made of a second tubular knitted fabric that is knitted in circular knitting continuously from the first anchor section 2 of the tubular knitted fabric, and which is knitted to be widened from one end 8a to the other end 8b of the second tubular knitted fabric.

The curling prevention section 8 is considered as being formed of, for example, a flexible amerib stitch knitted fabric.

Here, a float stitch knitted fabric is a knitted fabric in which a specific needle is put at an inoperative position during the knitting of a knitted fabric, so that knitting yarn is not fed to the needle and the previous loop is maintained, whereby knitting yarn of this portion floats straight on the back of the knitted fabric. In contrast, the amerib stitch knitted fabric is a float stitch knitted fabric in which a rubber thread knitted into a plain stitch knitted fabric is knitted to skip one course for every three courses.

Therefore, by making the curling prevention section 8 be the amerib stitch knitted fabric and making the first anchor section 2 be the moss stitch knitted fabric, it is possible to make the stretch resistance of the curling prevention section 8 in the circumferential direction H of the knee joint supporter 10 small with respect to the first anchor section 2.

That is, when the tension of the curling prevention section 8 in the circumferential direction H of the knee joint supporter 10 is set to be $F_{H8}$, the curling prevention section 8 has such a magnitude relation of $F_{H2} > F_{H8}$ that it has a weak tightening force in the circumferential direction H of the knee joint supporter 10, compared to the first anchor section.

In this manner, the curling prevention section 8 is a flexible knitted fabric and is knitted to be widened from one end 8a to the other end 8b of the second tubular knitted fabric, whereby in the case of wearing the knee joint supporter 10, the curling prevention section 8 fits to the surface (the inclined surface) of the thigh of a wearer, thereby following the movement of the thigh, and can prevent curling from one end 8a of the second tubular knitted fabric (the upper end 10a of the tubular knitted fabric).

In addition, the second embodiment is different from the first embodiment only in that the curling prevention section 8 is newly disposed at the first anchor section 2 of the knee joint supporter 10, and except the operation and effects by the curling prevention section 8 described above, the same operation and effects as those in the first embodiment are obtained.

(Third Embodiment of the Invention)

Figure 8B:
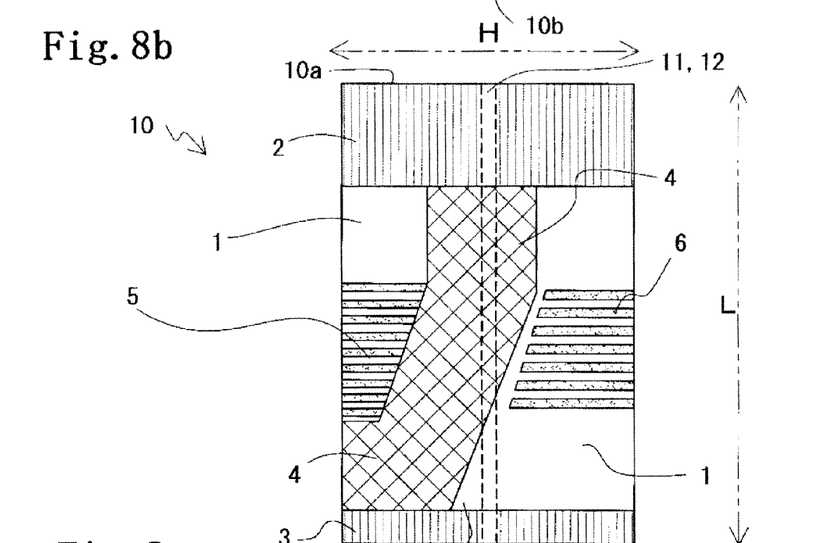
FIG. 8(b) is a right side view showing the schematic configuration of a knee joint supporter related to the third embodiment.
Figure 8C:
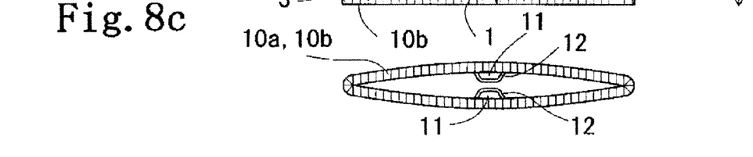
FIG. 8(c) is a plan view and bottom view of the knee joint supporter shown in FIG. 8(b).

FIG. 8(b) is a right side view showing the schematic configuration of a knee joint supporter related to the third embodiment, and FIG. 8(c) is a plan view and bottom view of the knee joint supporter shown in FIG. 8(b). In FIGS. 8(b) and 8(c) the same symbol as that in FIGS. 1, 2 and 6 or 7 denotes the same or equivalent section, and explanation thereof is omitted.

In FIG. 8(b) described above, the knee joint supporter 10 related to this embodiment is configured to have, in addition to the configuration in the first embodiment described above, an elastic bone member 11 which is formed of an approximately rod-shaped body having flexibility and resiliency and disposed at a given place of the knee joint supporter 10 to approximately conform a longitudinal direction thereof to the length direction L of the knee joint supporter 10 and have a length extending over approximately the entirety of the length direction L.

Further, the knee joint supporter 10 is configured to have a bag section 12 for accommodating and fixing the elastic bone member 11 provided inside the knee joint supporter 10.

The bag section 12 is constituted by disposing an elongated tape-shaped body made of a knitted fabric having excellent stretching properties at a given position of the inner surface of the knee joint supporter 10 that becomes a side portion of the knee in a wearing state of the knee joint supporter 10, in such a manner that a longitudinal direction thereof conforms to the length direction L of the knee joint supporter 10, and sewing a peripheral portion of the tape-shaped body to the knee joint supporter 10 to form an elongated bag-shaped space capable of accommodating and fixing the elastic bone member 11.

The elastic bone member 11 is configured to be formed as an elongated and approximately plate-shaped material which has flexibility and resiliency and has a length extending over approximately the entirety of the length direction L of the knee joint supporter 10 and in which a dimension in a width direction making a right angle with a thickness direction in a cross-sectional shape is large with respect to a dimension in the thickness direction. Specifically, a member generally superimposed on each other and mutual loop-shaped portions flattened into an elongated and approximate plate shape in a state where they are alternately intertwined is used.

The elastic bone member 11 is disposed by, after the bag section 12 is formed between the tape-shaped body and the knee joint supporter 10 by sewing the tape-shaped body to the knee joint supporter 10, accommodating the elastic bone member 11 in the bag section 12 in a direction in which the thin thickness direction of the elastic bone member 11 conforms to the thickness direction of the knee joint supporter 10 and the width direction of the elastic bone member 11 conforms to the circumferential direction L of the knee joint supporter 10, and fixed to a position corresponding to the side portion of the knee in the knee joint supporter 10.

Then, The elastic bone member 11 is a mechanism which permits the flexion and extension of the knee joint supporter 10 associated with normal flexion and extension of the knee joint, and on the other hand, suppresses motion other than a flexion change corresponding to the flexion and extension of the knee joint as far as possible, thereby preventing excessive force from being applied to the knee, and protecting the knee, along with the knee joint supporter 10 which imparts a tightening force as a whole.

In addition, as the elastic bone member 11, in addition to the coil bone, a rod-shaped body made of another elastic material such as plastics can also be used.

Further, in a state where the knee joint supporter 10 is worn, as long as the size of the knee joint supporter 10 fits the leg of a wearer, each knitted fabric of the knee joint supporter 10 appropriately expands and contracts, thereby properly coming into close contact with the knee region, and each of the elastic bone members 11 disposed on both left and right sides of the knee joint supporter 10 also enters a state of close contact along the side face of the knee of the wearer due to moderate elasticity thereof. Further, the outer shapes of the knee joint supporter 10 and the elastic bone member 11 does not stand out on the surface of outer clothes.

Further, each knitted fabric of the knee joint supporter 10 comes into close contact with the knee region of a wearer and two left and right elastic bone members 11 of the knee joint supporter 10 are also located at the sides of the knee of the wearer, thereby limiting unnecessary motion at the time of the flexion and extension of the knee joint, whereby an appropriate support state such as the knee being maintained in stable state can be always obtained. Further, the elastic bone member 11 is fixed to the knee joint supporter 10 in a state where the elastic bone member 11 has sufficiently secured a dimension in the circumferential direction H of the knee joint supporter 10, and generates a necessary resistance force or restoring force, thereby being able to appropriately support motion related to the flexion and extension of the knee joint, and the dimension of the elastic bone member 11 in the thickness direction of the knee joint supporter 10 is made small, whereby the elastic bone member 11 does not become bulky and does not cause an uncomfortable feeling in a wearing state.

As described above, in the knee joint supporter 10 related to this embodiment, the elastic bone member 11 which is disposed at the side portion is made of an elongated and approximately plate-shaped material and accommodated and disposed in the bag section 12 in a disposition state where the elastic bone member 11 becomes thin in the thickness direction of the knee joint supporter 10 and thick in the circumferential direction H of the knee joint supporter 10. Then, while allowing an elastic force in the circumferential direction H of the knee joint supporter 10 which is important for the flexion and extension of the knee joint be secured, with respect to the thickness direction of the knee joint supporter 10 which is less involved in the flexion and extension of the knee joint, the elastic bone member 11 is made to have a minimum necessary thickness. In this way, the occupied space of the elastic bone member 11 can be reduced while securing a certain resistance force to the flexion and a sufficient restoring force for the extension, so that the elastic bone member 11 does not become bulky at the side portion of the knee joint supporter 10, thereby being unable to affect outer clothes, and also an uncomfortable feeling due to the elastic bone members 11 on both sides of the knee is reduced at the time of the flexion and extension of the knee joint, so that the feeling of wearing can be improved.

Further, since the elastic bone member 11 is formed of an approximately rod-shaped body having flexibility and resiliency and disposed at a given place of the knee joint supporter 10 to approximately conform a longitudinal direction thereof to the length direction L of the knee joint supporter 10 and have a length extending over approximately the entirety of the length direction L, it is possible to prevent curling from the upper end 10a and the lower end 10b of the knee joint supporter 10.

In addition, in the knee joint supporter 10 related to this embodiment, a configuration is taken in which the bag sections 12 are respectively provided at two places on the inner surface side of the knee joint supporter 10, which become the side portions of the knee in a wearing state, and the elastic bone members 11 are accommodated and disposed in the bag sections 12. However, it is not limited to this configuration. For example, a configuration can also be taken in which each bag section 12 is provided on the outer surface side of the knee joint supporter 10 and each elastic bone member 11 is disposed at the outside of the knee joint supporter 10, so that it is possible to further reduce an uncomfortable feeling due to the elastic bone members 11 on both sides of the knee at the time of the flexion and extension of the knee joint. Further, the number of elastic bone members 11 is not limited to two, and a configuration in which only one elastic bone member 11 is disposed at any one of places which become the side portions of the knee in a wearing state of the knee joint supporter 10 or a configuration in which a plurality of elastic bone members 11 is disposed side by side at places which become the side portions of the knee, thereby strengthening a supporting force by two or more the elastic bone members 11, can also be taken.

Further, in the knee joint supporter 10 related to this embodiment, a configuration is taken in which the elastic bone members 11 are disposed at two places of the knee joint supporter 10, which become the side portions of the knee in a wearing state. However, it is not limited to this configuration. For example, an approximately rod-shaped elastic bone member 11 is formed by impregnating a given site of the main body of the knee joint supporter 10 with a liquid resin material which becomes an elastic resin body having flexibility and resiliency after curing, in the form of a line or a strip, and then curing this, thereby integrating this with the knitted fabric of the main body of the knee joint supporter 10. In this way, a configuration of functioning similarly to the elastic bone member 11 made of the coil bone in this embodiment can also be taken, and similarly to this embodiment, the elastic bone member 11 does not become bulky at the side portion of the knee joint supporter 10 while securing a certain resistance force to the flexion of the knee joint and a sufficient restoring force for the extension, and does not affect outer clothes.

In addition, the third embodiment is different from the first embodiment only in that the elastic bone member 11 and the bag section 12 are newly disposed at the side portion of the knee joint supporter 10, and except the operation and effects by the elastic bone member 11 described above, the same operation and effects as those in the first embodiment are obtained.

REFERENCE SIGNS LIST

1: base fabric section
2: first anchor section
3: second anchor section
4: supporting section
5: patella corresponding section
6: popliteal fossa contact section
7: knitted fabric of a boundary
8: curling prevention section
8*a*: one end
8*b*: other end
10: knee joint supporter
10*a*: upper end
10*b*: lower end
11: elastic bone member
12: bag section

The invention claimed is:

1. A knee joint supporter constructed from a tubular knitted fabric that is knitted by circular knitting, and adapted to come into close contact with a body surface of a wearer, thereby assisting a knee joint by improving the stability thereof, the knee joint supporter comprising:
    a first anchor section which is knitted around an upper end of the tubular knitted fabric and adapted to allow the tubular knitted fabric to be tightened on a thigh of the wearer;
    a second anchor section which is knitted around a lower end of the tubular knitted fabric and adapted to allow the tubular knitted fabric to be tightened on a lower thigh of the wearer;
    a base fabric section having stretching properties that is knitted in an area between the first anchor section and the second anchor section of the tubular knitted fabric;
    a patella corresponding section which is knitted on a front face side of the tubular knitted fabric and is adapted to receive a patella of the wearer; and
    a supporting section which is knitted in an approximate U-shape that is connected to the first anchor section and is adapted to surround a section corresponding to the patella of the wearer and to support the patella of the wearer,
    wherein stretch resistances of the first anchor section and the second anchor section in a circumferential direction of the tubular knitted fabric are larger than a stretch resistance of a base fabric section in the circumferential direction of the tubular knitted fabric,
    a stretch resistance of the supporting section in a length direction of the tubular knitted fabric is larger than a stretch resistance of the base fabric section in the length direction of the tubular knitted fabric, and
    wherein a stretch resistance of the patella corresponding section in the length direction of the tubular knitted fabric is smaller than the stretch resistance of the base fabric section in the length direction of the tubular knitted fabric.

2. The knee joint supporter according to claim 1, wherein the supporting section is connected to the second anchor section and extends between the first anchor section and the second anchor section and is adapted to support a medial collateral ligament and a lateral collateral ligament of the wearer.

3. The knee joint supporter according to claim 2, further comprising:
    a popliteal fossa contact section which is knitted on a rear face side of the tubular knitted fabric and is adapted to contact the popliteal fossa of the wearer,
    wherein a stretch resistance of the popliteal fossa contact section in the length direction of the tubular knitted fabric is smaller than the stretch resistance of the base fabric section in the length direction of the tubular knitted fabric.

4. The knee joint supporter according to claim 2, further comprising:
    a curling prevention section which is made of a second tubular knitted fabric that is knitted in circular knitting continuously from the first anchor section of the tubular knitted fabric, and which is knitted to be widened from one end to the other end of the second tubular knitted fabric,
    wherein a stretch resistance of the curling prevention section in the circumferential direction of the tubular knitted fabric is smaller than the stretch resistance of the first anchor section in the circumferential direction of the tubular knitted fabric.

5. The knee joint supporter according to claim 2, further comprising:
    a bag section which is disposed at one of an inner surface side or an outer surface side of the tubular knitted fabric; and
    an elastic bone member which is accommodated in the bag section, is formed of an approximately rod-shaped body having flexibility and resiliency, and is disposed at a given place of the tubular knitted fabric to approximately conform a longitudinal direction thereof to the length direction of the tubular knitted fabric and have a length extending over approximately the entirety of the length direction.

6. The knee joint supporter according to claim 1, wherein the base fabric section is continuous from a rear face side of the tubular knitted fabric and is knitted to be interposed between the supporting section and the second anchor section.

7. The knee joint supporter according to claim 6, further comprising:
a popliteal fossa contact section which is knitted on a rear face side of the tubular knitted fabric and adapted to contact the popliteal fossa of the wearer,
wherein a stretch resistance of the popliteal fossa contact section in the length direction of the tubular knitted fabric is smaller than the stretch resistance of the base fabric section in the length direction of the tubular knitted fabric.

8. The knee joint supporter according to claim 6, further comprising:
a curling prevention section which is made of a second tubular knitted fabric that is knitted in circular knitting continuously from the first anchor section of the tubular knitted fabric, and which is knitted to be widened from one end to the other end of the second tubular knitted fabric,
wherein a stretch resistance of the curling prevention section in the circumferential direction of the tubular knitted fabric is smaller than the stretch resistance of the first anchor section in the circumferential direction of the tubular knitted fabric.

9. The knee joint supporter according to claim 6, further comprising:
a bag section which is disposed at one of an inner surface side or an outer surface side of the tubular knitted fabric; and
an elastic bone member which is accommodated in the bag section, is formed of an approximately rod-shaped body having flexibility and resiliency, and is disposed at a given place of the tubular knitted fabric to approximately conform a longitudinal direction thereof to the length direction of the tubular knitted fabric and have a length extending over approximately the entirety of the length direction.

10. The knee joint supporter according to claim 1, wherein a knitted fabric of a boundary between the supporting section and the patella corresponding section is knitted by overlapping an upper thread which is used in the supporting section and an upper thread which is used in the patella corresponding section and using the upper threads along with a common under thread which is used in the supporting section and the patella corresponding section.

11. The knee joint supporter according to claim 10, further comprising:
a popliteal fossa contact section which is knitted on a rear face side of the tubular knitted fabric and adapted to contact the popliteal fossa of the wearer,
wherein a stretch resistance of the popliteal fossa contact section in the length direction of the tubular knitted fabric is smaller than the stretch resistance of the base fabric section in the length direction of the tubular knitted fabric.

12. The knee joint supporter according to claim 1, further comprising:
a popliteal fossa contact section which is knitted on a rear face side of the tubular knitted fabric and is configured to contact a popliteal fossa of the wearer,
wherein a stretch resistance of the popliteal fossa contact section in the length direction of the tubular knitted fabric is smaller than the stretch resistance of the base fabric section in the length direction of the tubular knitted fabric.

13. The knee joint supporter according to claim 1, further comprising:
a curling prevention section which is made of a second tubular knitted fabric that is knitted in circular knitting continuously from the first anchor section of the tubular knitted fabric, and which is knitted to be widened from one end to the other end of the second tubular knitted fabric,
wherein a stretch resistance of the curling prevention section in the circumferential direction of the tubular knitted fabric is smaller than the stretch resistance of the first anchor section in the circumferential direction of the tubular knitted fabric.

14. The knee joint supporter according to claim 1, further comprising:
a bag section which is disposed at one of an inner surface side or an outer surface side of the tubular knitted fabric; and
an elastic bone member which is accommodated in the bag section, is formed of an approximately rod-shaped body having flexibility and resiliency, and is disposed at a given place of the tubular knitted fabric to approximately conform to a longitudinal direction thereof to the length direction of the tubular knitted fabric and have a length extending over approximately the entirety of the length direction.

* * * * *